United States Patent [19]

Noorlander et al.

[11] Patent Number: 4,668,692
[45] Date of Patent: May 26, 1987

[54] DRY POWDERED GERMICIDE AND HEALING COMPOSITIONS

[76] Inventors: Daniel O. Noorlander, 508 W. 630 South, Orem, Utah 84057; Richard A. Heckmann, 603 E. 4300 North, Provo, Utah 84601

[21] Appl. No.: 830,486

[22] Filed: Feb. 18, 1986

Related U.S. Application Data

[63] Continuation of Ser. No. 607,707, May 7, 1984, abandoned.

[51] Int. Cl.$^4$ .................... A61K 31/415; A61K 31/34
[52] U.S. Cl. ...................................... 514/390; 514/474
[58] Field of Search ................................ 514/390, 474

[56] References Cited

U.S. PATENT DOCUMENTS

| | | | |
|---|---|---|---|
| 3,296,078 | 1/1967 | Kaye | 424/273 |
| 3,681,492 | 8/1972 | Kotzbauer | 424/280 |
| 3,950,554 | 4/1976 | Prince | 424/273 |
| 3,954,989 | 5/1976 | Mecca | 424/273 |
| 4,178,372 | 12/1979 | Coats | 424/364 |
| 4,244,963 | 1/1981 | Grier et al. | 424/263 |

OTHER PUBLICATIONS

Chemical Abstracts; vol. 89, (1978), #152595y; Anon.
Chemical Abstracts; vol. 95, (1981), #209692h; Carlhian.
Chemical Abstracts; vol. 66, (1967), #49224c; Kaye et al.
The Merck Index, 10th Edition, (1983), p. 844-filed in parent application 06/607,707.

Primary Examiner—Leonard Schenkman
Assistant Examiner—Joseph A. Lipovsky
Attorney, Agent, or Firm—Thorpe, North & Western

[57] ABSTRACT

Nontoxic, dry, powdered germicide, and healing compositions are disclosed comprising allantoin, ascorbic acid and an inert powdered carrier.

4 Claims, No Drawings

4,668,692

DRY POWDERED GERMICIDE AND HEALING COMPOSITIONS

This is a continuation of application Ser. No. 607,707, filed 5-7-84, now abandoned.

BACKGROUND OF THE INVENTION

1. Field

The invention relates to non-toxic, germicide and healing compositions, and in particular, to such compositions which are adapted for topical application to dairy cattle and other domesticated farm animals.

2. State of the Art

Comfrey (Symphytum officinale) has been reported in old herbal books as far back as 200 A.D. as a valuable medicinal herb to encourage epithelial formation in wounds, ulcers, and osteomyelitis. An evaluation of the plant by many investigators has disclosed that allantoin, a diureide of glyoxylic acid is the active ingredient found in the comfrey plant that increases the granulation of damaged tissue in the healing process. Allantoin can also be formed by the oxidation of uric acid in most mammals except man and anthropoid apes. Extensive use, however, of the comfrey plant or of its active ingredient, allantoin, has not been employed in either human medical treatment or in the area of veterinary medicine.

OBJECTIVES

A principal objective of the present invention is to provide an effective germicide and healing composition which can be used in veterinary medicine, particularly as a sterile, topical dressing for infections in dairy cattle and in treating burns, sores, and cuts and abrasions in domesticated farm animals. An additional objective of the present invention is to provide a composition which is active in killing infectious microorganisms such as Staphylococcal and Streptococcal bacteria. A particular objective of the present invention is to provide a non-toxic, topical dressing which kills many types of pathogenic bacteria on the surface of the skin tissue while at the same time effecting a rapid healing of the damaged tissue. Another objective is to provide a non-toxic, germicide, and healing composition which can be used as a topical dressing for application to dairy cattle in the prevention of mastitis.

SUMMARY OF THE INVENTION

The above objectives are achieved in accordance with the present invention by providing a novel, non-toxic, germicide, and healing composition comprising allantoin, ascorbic acid, and an inert, powdered carrier. The carrier can be any solid material which when applied in powdered form is inert to the skin and teats of dairy animals and other form animals. The carrier is preferably a member selected from the group consisting of talc, corn starch, and mixtures thereof. The concentration of the allantoin is from about 3 to 15% by weight, with the concentration of ascorbic acid being from about 7% to 25% by weight. In a preferred embodiment of the invention, the non-toxic germicide, and healing composition includes from about 6% to 12% by weight allantoin and from about 10% to 20% by weight ascorbic acid. The composition containing the allantoin, ascorbic acid and a carrier, such as talc and/or corn starch, in accordance with the present invention can be produced by simply mixing the separate ingredients together.

The present invention provides a dry composition in which the carrier is effective in holding the active ingredients on the skin surface. The composition is particularly adapted to be used during cold and wet winter months on the teats of cows. The dry composition is, of course, effective and advantageously used throughout the year. In the cold winter months, however, the dry composition is particularly advantageous. A wet composition applied to the teats of cows during wet and cold atmospheric conditions can cause chapping and frost damage of the teats. The dry composition does not have any such deleterious effect, and a 90% or better reduction in bacteria numbers on the teats of cows treated with the dry composition can be achieved in only 30 minutes' treatment with the composition.

DETAILED DESCRIPTION OF THE PREFERRED EMBODIMENTS

Additional objects and features of the invention will become apparent from the following detailed description which describe in particular, preferred embodiments of the invention representing the best mode presently contemplated of carrying out the invention.

In accordance with the invention, a non-toxic, germicide, and healing composition is provided comprising, allantoin ascorbic acid, and a carrier comprising a member selected from the group consisting of talc, corn starch, and mixtures thereof. The concentration of allantoin is between 3% and 15% by weight and preferably between about 6% and 12% by weight. The concentration of ascorbic acid is between about 7% and 25% by weight and preferably between about 10% and 20% by weight. It has been found that the dry composition containing allantoin, ascorbic acid and the carrier is effective in killing many types of bacteria when applied to skin or tissue in which the bacteria are found. In addition, the application of the composition accelerates the healing process for cuts, cracks, etc. in the skin tissue.

One of the major advantages of the composition of the present invention is that it provides for an alternative method of treating dairy animals for mastitis whereby antibiotics are not required. Mastitis is a major bacteria disease of dairy animals which is caused by several types of bacteria including Pseudomonas, Staphylococcus and Streptococcus. Extensive testing was done to determine the bacteriocide and healing properties of the dry composition of the present invention. Laboratory experiments have shown conclusively that the compositions of this invention are very effective in killing those type bacteria.

A dry composition containing 10% to 15% ascorbic acid, 3% to 6% allantoin and the remainder being essentially talc was applied as a topical agent to the teats of several cows which showed symptoms of mastitis. As can be seen from the results as summarized in Table 1, a 90% or better reduction in the number of bacteria was achieved within 30 minutes after application. The application was repeated twice daily for two or three days and the cows responded exceptionally well to the treatment. In essentially all instances, the teats of the cows no longer showed pressure of mastitis causing bacteria.

TABLE I

| Cow No. | Type of Sample | Time From Treatment (Min.) | Total Bacteria (Counts × 1000) | Total Cocci | Percent Reduction All Bacteria | Percent Reduction Cocci |
|---|---|---|---|---|---|---|
| 1 | Swab | 0 | 1707 | 435 | | |
| | | 30 | 417 | 39 | 76 | 91 |
| | Contact Plate | 0 | 320 | 183 | | |
| | | 30 | 61 | 14 | 81 | 91 |
| 2 | Swab | 0 | 57 | 34 | | |
| | | 30 | 11 | 3 | 80 | 92 |
| | Contact Plate | 0 | 149 | 133 | | |
| | | 30 | 9 | 7 | 94 | 95 |
| 3 | Swab | 0 | 1062 | 992 | | |
| | | 30 | 35 | 9 | 97 | 99 |
| | Contact Plate | 0 | 127 | 59 | | |
| | | 30 | 17 | 6 | 87 | 90 |

In a similar test, a dry composition containing 10% to 15% ascorbic acid, 7% to 10% allantoin and the remainder being essentially corn starch was applied to the teats of several cows which showed symptoms of mastitis. Results, as summarized in Table 2, were similar to those achieved with the composition containing the dry talc carrier. In Table 2, the number of bacteria colonies are represented by a scale of 5 being too numerous to count, 0 being no colonies.

TABLE 2

| Cow Number | Time From Treatment (Min.) | Number of Bacteria Colonies |
|---|---|---|
| 4 | 0 | 5 |
| | 30 | 2–3 |
| | 45 | 1 |
| 5 | 0 | 4–6 |
| | 30 | 0–1 |
| | 45 | 0 |
| 6 | 0 | 4–5 |
| | 30 | 0–1 |
| | 45 | 0–1 |

One benefit which has been found with the composition containing corn starch as the carrier material is that the corn starch is less irritating to an open cut or incisions on the animal's skin. In controlled tests in which incisions were made in the test animals, it was found that the incisions treated with a composition containing the active ingredients (ascorbic acid and allantoin) in an inert corn starch carrier healed and closed over somewhat more rapidly than incisions treated with a composition containing the same concentration of active ingredients in an inert talc carrier.

Laboratory testing has demonstrated that the compositions of the invention have excellent kill properties as to various bacteria. Staphylococcal, Streptococcal, yeast, coliform, pseudomona, and some fungal microorganisms could be killed in as little as 10 to 45 minutes. Rod shaped organisms with spores are not killed as rapidly as the spherical shaped streptococcal and staphylococcal bacteria, but the composition does act to kill such organisms.

Although preferred embodiments of the invention have been disclosed, it is to be understood that various changes and modifications can be made without departing from the subject matter coming within the scope of the following claims, which subject matter is regarded as the invention.

We claim:

1. A dry, non-toxic, germicide, and healing composition comprising allantoin, ascorbic acid, and an inert, powered carrier, with the allantoin being present in an amount of from about 6% to about 12% by weight, and with the ascorbic acid being present in an amount of from about 10% to about 20% by weight.

2. A dry, non-toxic, germicide, and healing composition in accordance with claim 1, wherein the inert carrier is a member selected from the group consisting of talc, corn starch, and mixtures thereof.

3. A method of treating udders of domesticated farm animals to reduce infectious bacteria thereon, said method comprising applying topically to the tests of the udder an effective amount of a dry, non-toxic, germicide, and healing composition comprising allantoin, ascorbic acid, and an inert, powdered carrier, with the allantoin being present in said composition in an amount of from about 6% to about 12% by weight, and with the ascorbic acid being present in said composition in an amount of from about 10% to about 20% by weight.

4. A method in accordance with claim 3, wherein the inert carrier is a member selected from the group consisting of talc, corn starch, and mixtures thereof.

* * * * *